(12) United States Patent
Cho et al.

(10) Patent No.: US 7,799,441 B2
(45) Date of Patent: *Sep. 21, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Min Jeong Lee, Seoul (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 681 days.

This patent is subject to a terminal disclaimer.

(21) Appl. No.: 11/659,091

(22) PCT Filed: Sep. 23, 2005

(86) PCT No.: PCT/KR2005/003175

§ 371 (c)(1), (2), (4) Date: Feb. 1, 2007

(87) PCT Pub. No.: WO2006/080642

PCT Pub. Date: Aug. 3, 2006

(65) Prior Publication Data

US 2008/0303414 A1 Dec. 11, 2008

(30) Foreign Application Priority Data

Sep. 24, 2004 (KR) .................. 10-2004-0077245

(51) Int. Cl.
*H01L 51/54* (2006.01)
(52) U.S. Cl. .............. 428/690; 428/917; 313/504; 313/506; 252/301.16; 257/40; 257/E51.032; 546/15; 546/16; 546/18; 556/408
(58) Field of Classification Search .......... 556/408
See application file for complete search history.

(56) References Cited

U.S. PATENT DOCUMENTS

| | | | |
|---|---|---|---|
| 6,605,373 B2 | 8/2003 | Woo et al. | |
| 6,613,454 B2 | 9/2003 | Ara et al. | |
| 6,630,254 B2 | 10/2003 | Leclerc et al. | |
| 2004/0219386 A1 | 11/2004 | Thoms | |

FOREIGN PATENT DOCUMENTS

| | | |
|---|---|---|
| EP | 1 310 539 B1 | 3/2005 |
| JP | 2008-510800 | 4/2008 |
| JP | 2008-511157 | 4/2008 |
| JP | 2008-511159 | 4/2008 |
| JP | 2008-511160 | 4/2008 |
| WO | WO 93/09074 | 5/1993 |
| WO | WO 2006/080640 | 8/2006 |
| WO | WO 2006/080641 | 8/2006 |
| WO | WO 2006/080642 | 8/2006 |
| WO | WO 2006/080643 | 8/2006 |
| WO | WO 2006/080644 | 8/2006 |

OTHER PUBLICATIONS

W. Tritschler, *Synthese un Konformation von Spiroacridanen*, Chem. Ber. 117, pp. 2703-2713; 1984.
Patrick Keller, "Photo-Cross-Linkable Liquid-Crystalline Side-Chain Polysiloxanes", Chemistry of Materials, vol. 2, pp. 3-4, 1990.
Geselowitz et al., "Quantitation of Triple-Helix Formation Using a Photo-Cross-Linkable Aryl Azide/Biotin/Oligonucleotide Conjugate", Bioconjugate Chem., vol. 6, pp. 502-506, 1995.

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

7 Claims, 1 Drawing Sheet

[Fig. 1]
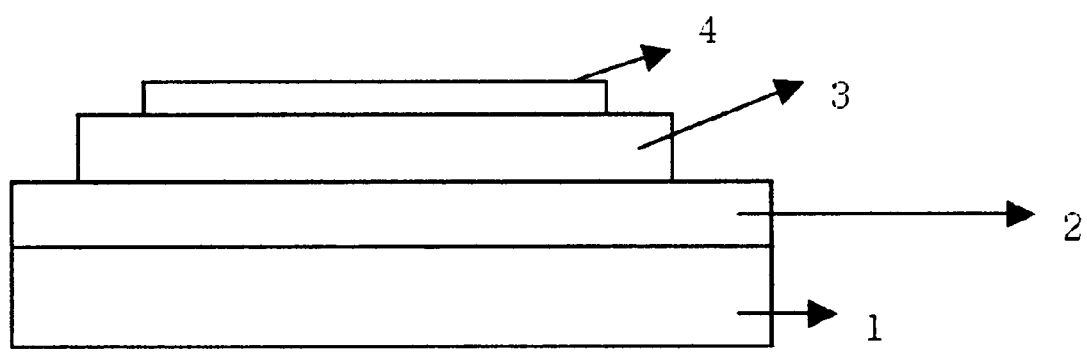
[Fig. 2]
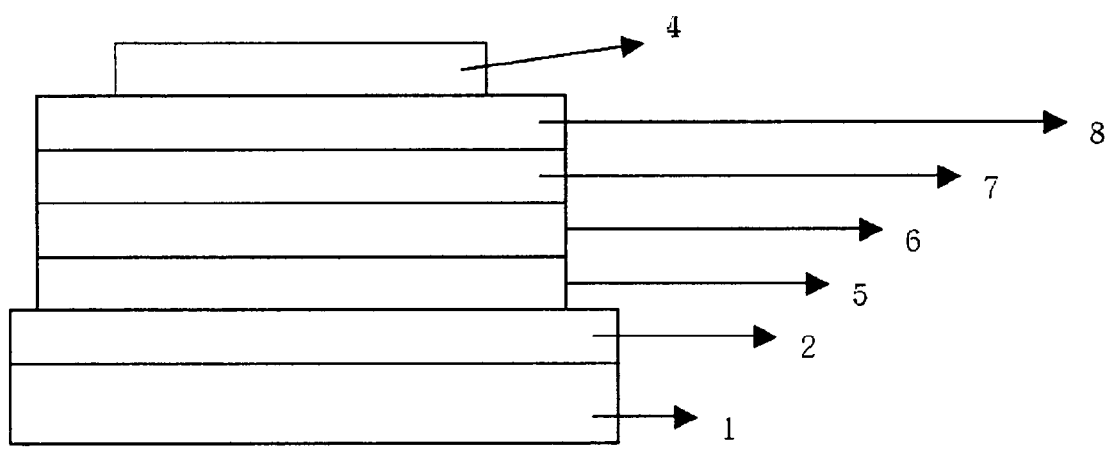

COMPOUND AND ORGANIC LIGHT EMITTING DEVICE USING THE SAME

This application claims priority to International Application No. 10-PCT/KR2005/003175, filed on Sep. 23, 2005, and Korean Patent Application No. 10-2004-0077245, filed on Sep. 24, 2004, which are hereby incorporated by reference in their entirety.

TECHNICAL FIELD

The present invention relates to an organic light emitting device which comprises a fluorene derivative capable of significantly improving a lifespan, efficiency, and electrochemical and thermal stabilities thereof.

BACKGROUND ART

An organic light emission phenomenon is an example of a conversion of current into visible rays through an internal process of a specific organic molecule. The organic light emission phenomenon is based on the following mechanism. When an organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

[Formula 1]

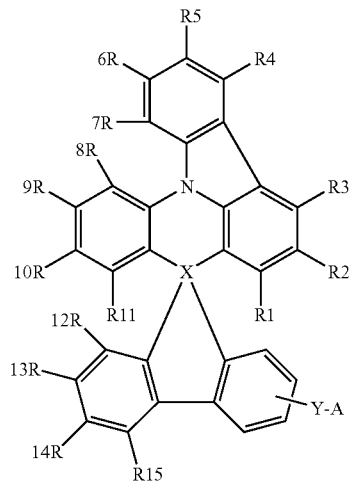

In Formula 1, X is C or Si, and A is —NZ1Z2.

Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Z1 and Z2 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons.

R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group. R1 to R11 may form aliphatic or hetero condensation rings along with adjacent groups.

R12 to R15 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group. R12 to R15 may form aliphatic or hetero condensation rings along with adjacent groups.

R7 and R8 may be directly connected to each other, or may form a condensation ring along with a group selected from the group consisting of O, S, NR, PR, C=O, CRR', and SiRR'. R and R' are each independently or collectively hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound.

A detailed description will be given of the substituent groups of Formula 1.

In Z1 and Z2 as the substituent groups of Formula 1, the aromatic hydrocarbons are exemplified by monocyclic aromatic rings, such as phenyl, biphenyl, and terphenyl, and multicyclic aromatic rings, such as naphthyl, anthracenyl, pyrenyl, and perylenyl. The heterocyclic group is exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R15 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R15 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R11 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R15 of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

In addition, illustrative, but non-limiting, examples of the alkenyl, aryl, arylamine, and heterocyclic groups of R1 to R15 of Formula 1 include groups shown in the following Formulae.

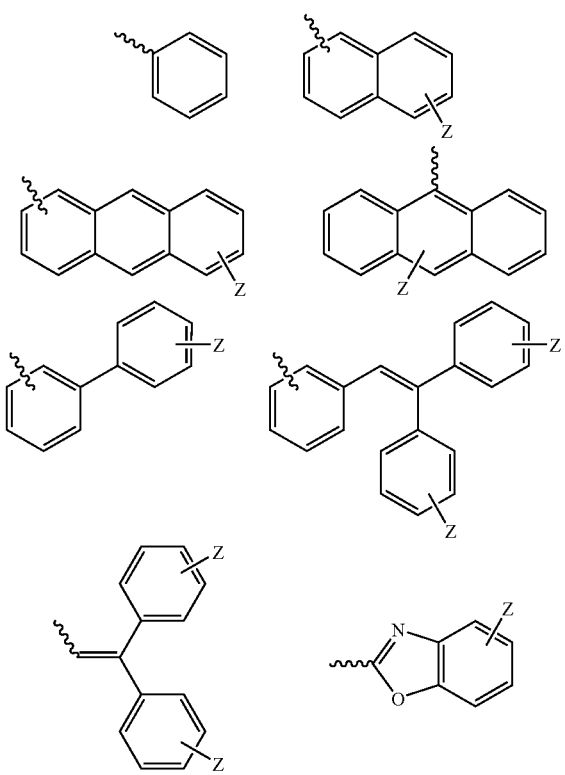

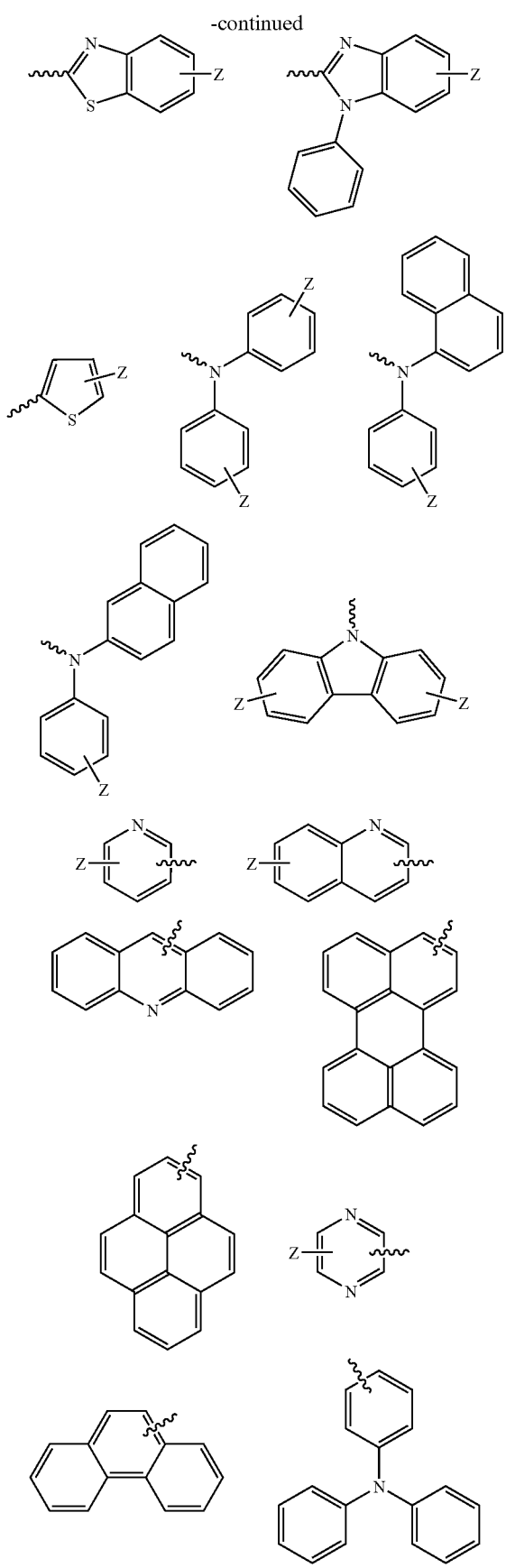

In the above Formulae, Z is a group selected from the group consisting of hydrogen, aliphatic hydrocarbons having a carbon number of 1-20, an alkoxy group, an arylamine group, an aryl group, a heterocyclic group, a nitrile group, and an acetylene group. Examples of the arylaamine, aryl, and heterocyclic groups of Z are as shown in the above-mentioned substituent groups of R1 to R15.

According to a preferred embodiment of the present invention, X of Formula 1 is C, and R7 and R8 are directly connected to each other, or form a condensation ring along with a group selected from the group consisting of O, S, NR, PR, C=O, CRR', and SiRR' (R and R' are as defined in Formula 1).

According to another preferred embodiment of the present invention, X of Formula 1 is Si, and R7 and R8 are directly connected to each other, or form a condensation ring along with a group selected from the group consisting of O, S, NR, PR, C=O, CRR', and SiRR' (R and R' are as defined in Formula 1).

According to still another preferred embodiment of the present invention, the compound of Formula 1 may be any one of Formulae 2 to 5.

[Formula 2]

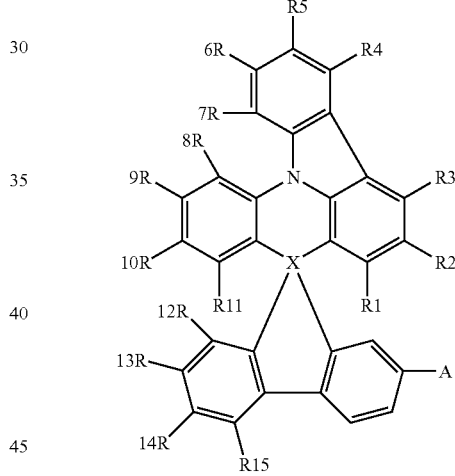

[Formula 3]

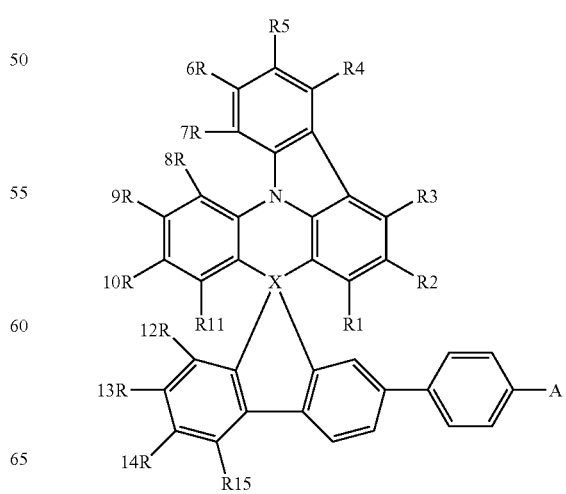

[Formula 4]

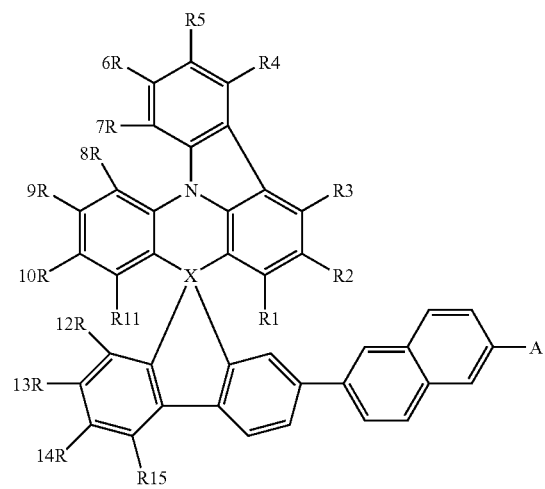

[Formula 5]

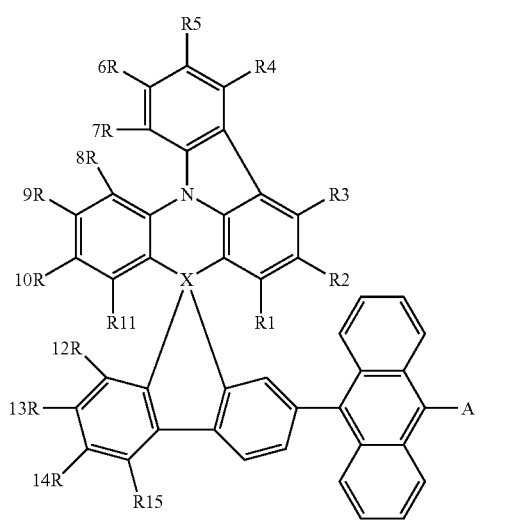

In the above Formulae, A is as defined in Formula 1.

Illustrative, but non-limiting, examples of the A group of Formula 1 are as follows. Combination of the compounds of Formulae 2 to 5 and the following group A can form various derivatives. For example, if the compound of Formula 2 is combined with the group 1, the resulting product will be designated by the compound of Formula 2-1.

[A Group]

1

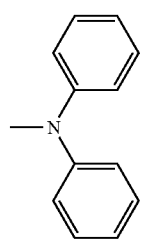

2

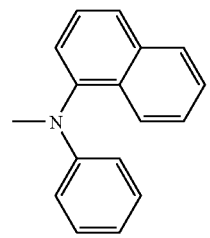

3

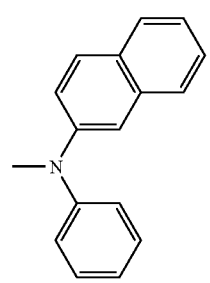

4

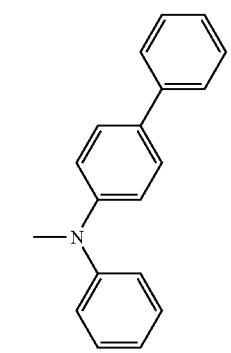

5

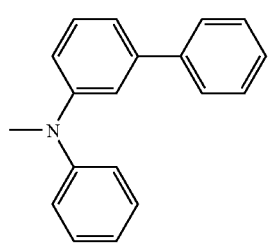

6

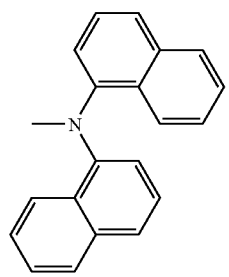

-continued
7
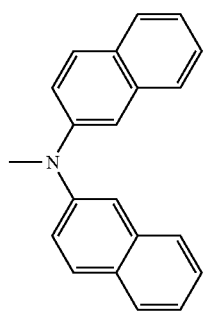
8
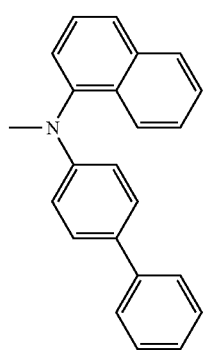
9
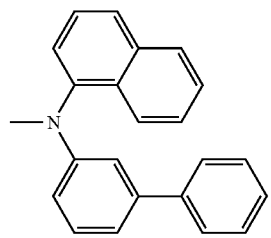
10
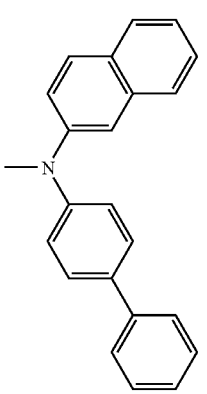
11
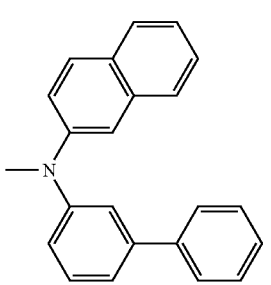
-continued
12
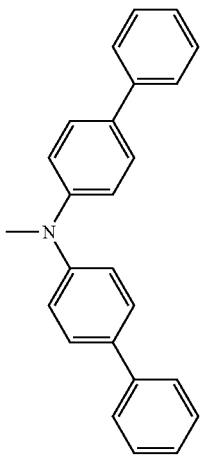
13
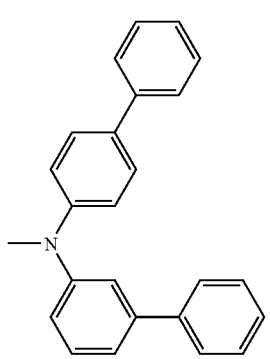
14
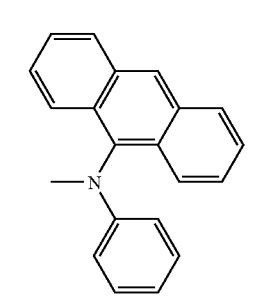
15
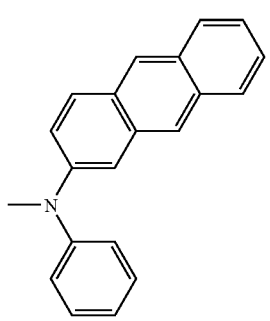

-continued
16
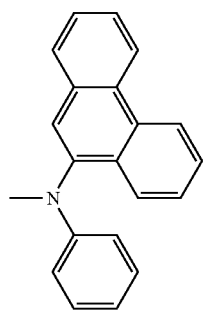
17
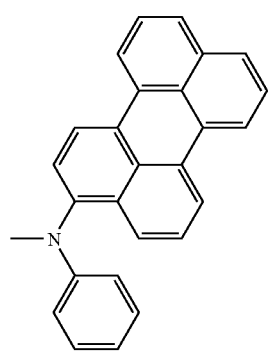
18
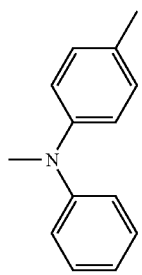
19
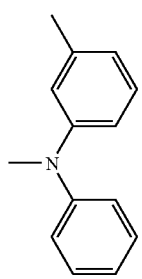
20
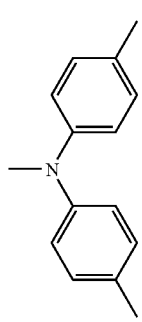
-continued
21
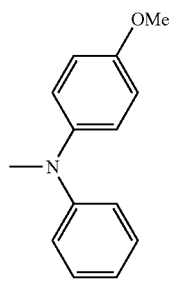
22
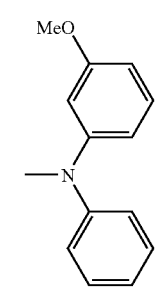
23
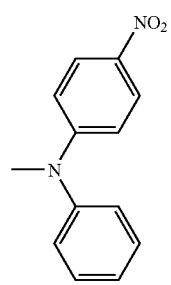
24
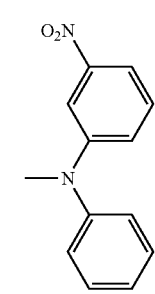
25
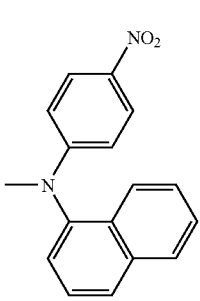

-continued
26
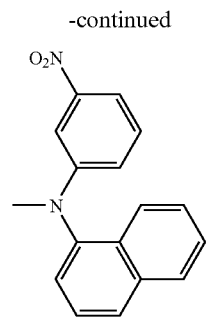
27
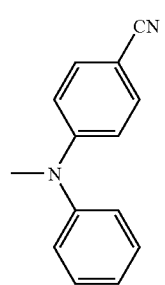
28
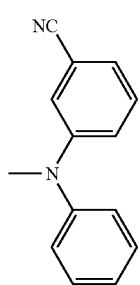
29
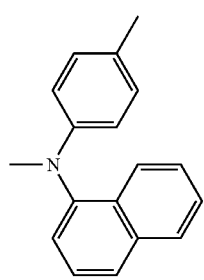
30
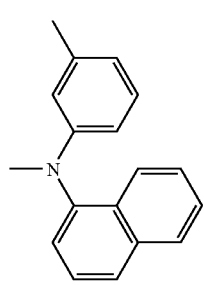
-continued
31
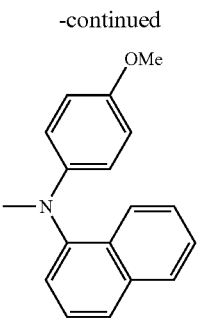
32
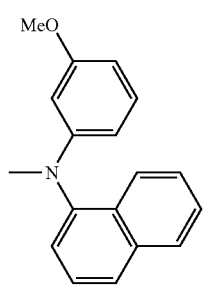
33
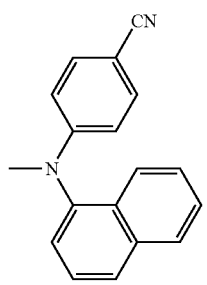
34
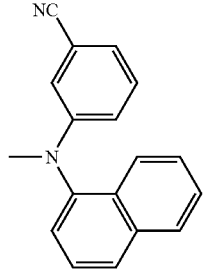
35
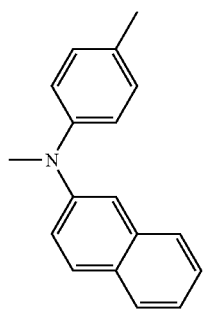

-continued
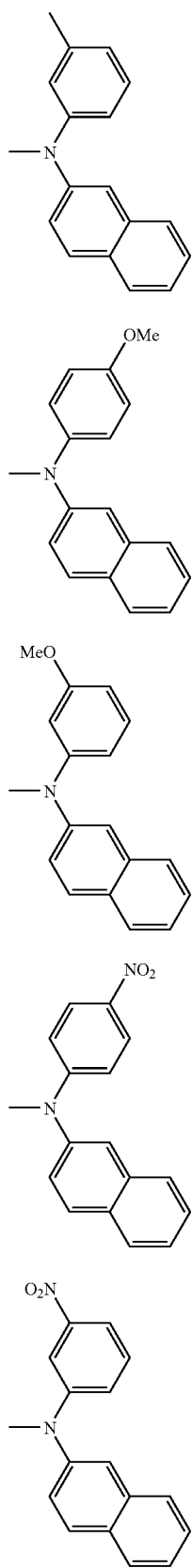
36
37
38
39
40
-continued
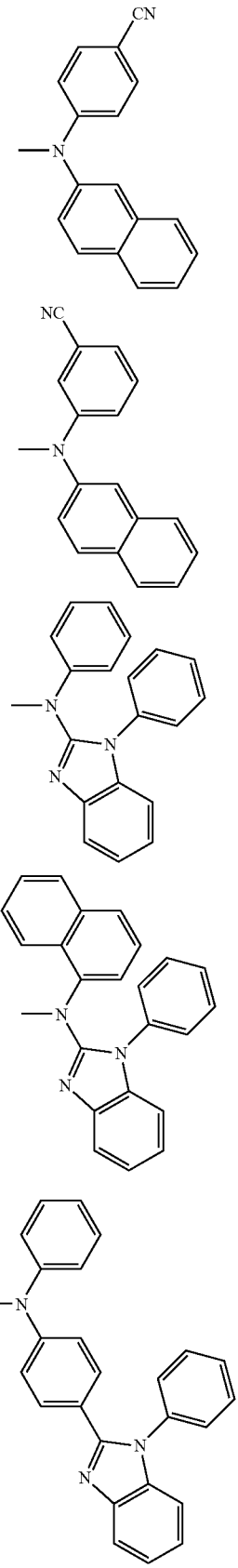
41
42
43
44
45

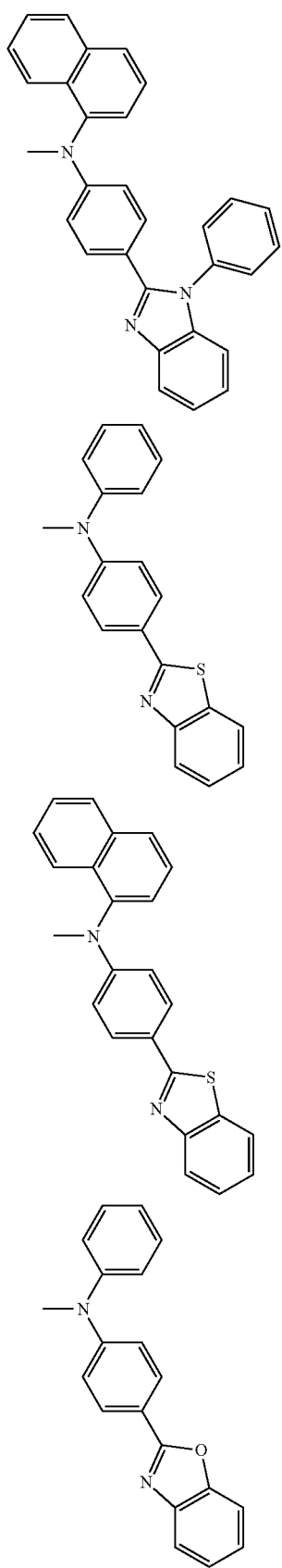
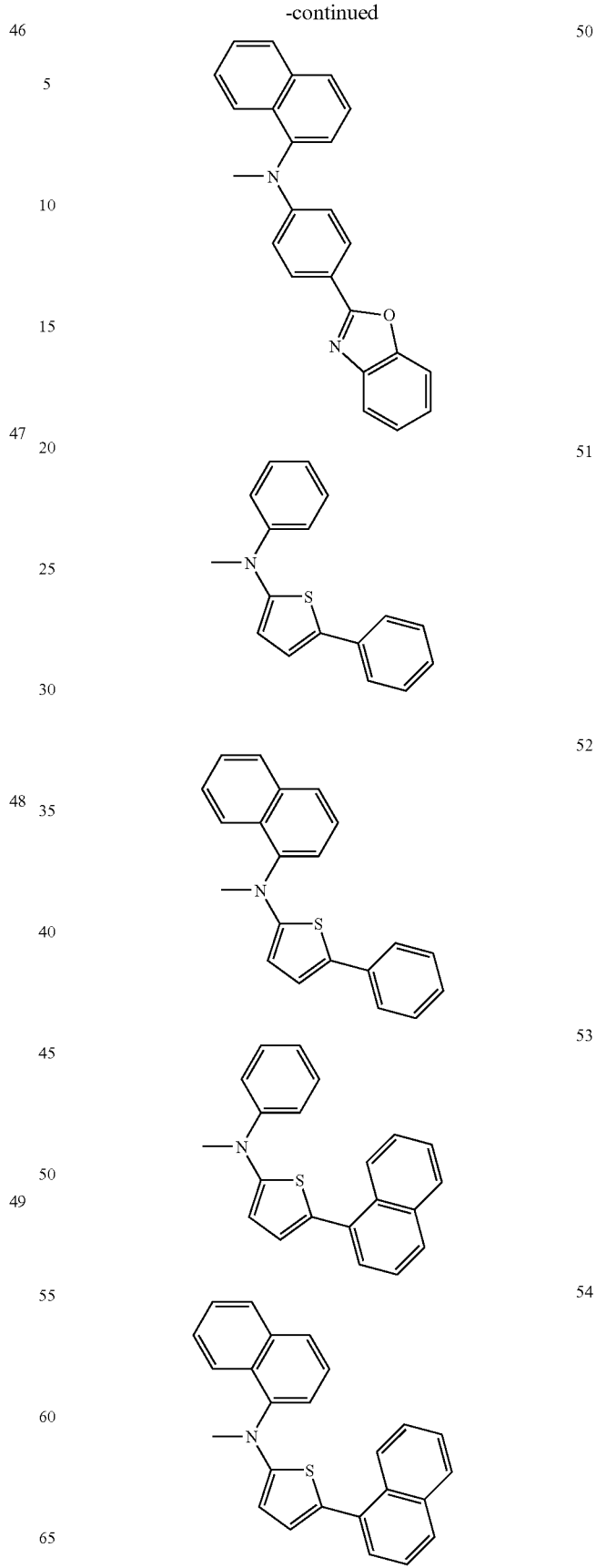

-continued

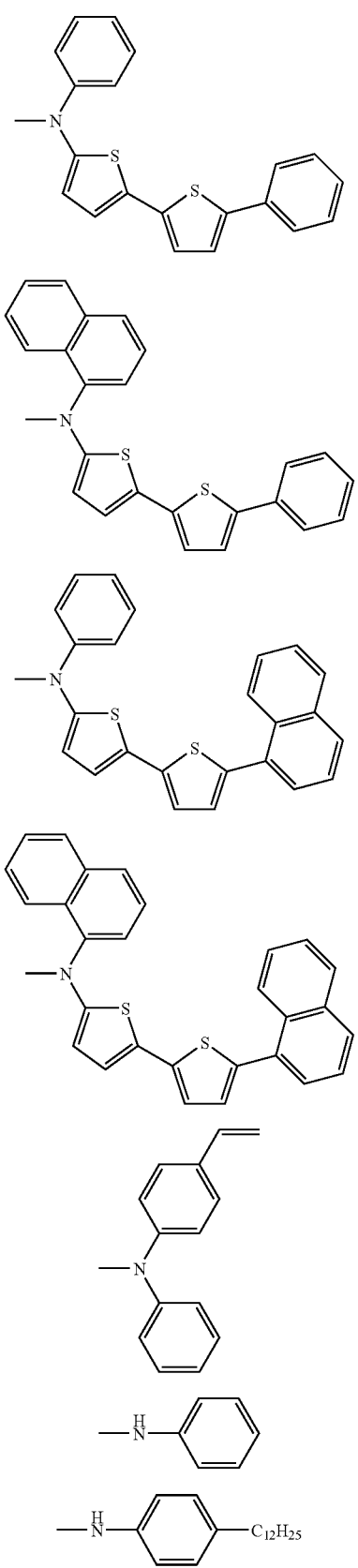

BRIEF DESCRIPTION OF THE DRAWINGS

FIG. 1 illustrates an organic light emitting device comprising a substrate 1, an anode 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

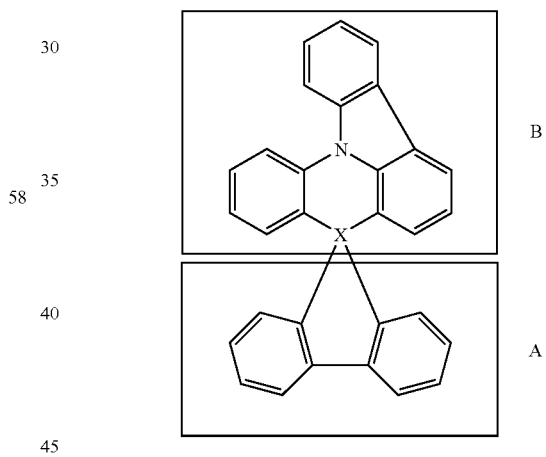

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R15 positions and Z1 and Z2 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap.

Furthermore, in the present invention, it is possible to control HOMO and LUMO energy levels of the compound by introducing various substituent groups into the R1 to R15 positions and the Z1 and Z2 positions of the core structure.

Additionally, by introducing various substituent groups into the core structure, compounds having intrinsic characteristics of the substituent groups can be synthesized. For example, substituent groups, which are frequently applied to hole injection layer materials, hole transport layer materials, light emitting layer materials, and electron transport layer materials which are used during the production of the organic light emitting device, are introduced into the core structure so as to produce substances capable of satisfying requirements of each organic material layer. For example, since the core structure of the compound of Formula 1 includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are asymmetrically introduced into the core structure (for example, the A portion is introduced into one side of the core structure) so as to precisely control the energy band gap, improve interfacial characteristics with organic materials, and apply the compound to various fields.

As well, if the number of amine contained in the substituent group A is set to 1 (if Z1 and Z2 are hetero aromatic amine compounds, the number of nitrogen contained in them is not counted), it is possible to precisely control the HOMO and LUMO energy levels and the energy band gap, and on the other hand interfacial characteristics with the organic materials is improved and thereby make it possible to apply the compound to various fields.

Additionally, various substituent groups are introduced into the steric structure of the compound of Formula 1 using spiro bonding to control the three-dimensional structure of the organic material so as to minimize $\pi$-$\pi$ interaction in the organic material, thereby formation of excimers is prevented.

With respect to the energy band gap and the energy level, for example, since the compound of Formula 2-1, in which arylamine is introduced into the hole transport material or the hole injection material of the structure of Formula 1, has HOMO of 5.47 eV, it has an energy level suitable for the hole injection layer or the hole transport layer. Meanwhile, the compound of Formula 2-2 has the band gap of 3.18 eV, which is still larger than that of NPB, typically used as the hole transport layer material, thus it has a LUMO value of about 2.29 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting device so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2-2, oxidation repeatedly occurs at the same voltage and the current amount is the same. This means that the compound has excellent stability to oxidation.

Meanwhile, since the compound of Formula 1 has a high glass transition temperature (Tg), it has excellent thermal stability. For example, the glass transition temperature of the compound of Formula 2-2 is 129° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 2-2 has excellent solubility to a polar solvent, such as xylene, dichloroethane, or NMP, which is used during the production of the device, and forms a thin film very well through the process using a solution, thus the solution coating process may be applied to produce the device. Additionally, a light emitting wavelength of a thin film or a solid formed using the solution coating process is typically shifted to a longer wavelength due to interaction between molecules, in comparison with a light emitting wavelength in a solution state. Little shift in the wavelength occurs in the compound having the structure shown in Formula 1.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

The organic light emitting device of the present invention can be produced using known materials through a known process, modified only in that at least one layer of organic material layer(s) includes the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, any one of the compounds of the following Formulae, a to c, may be used as a starting material.

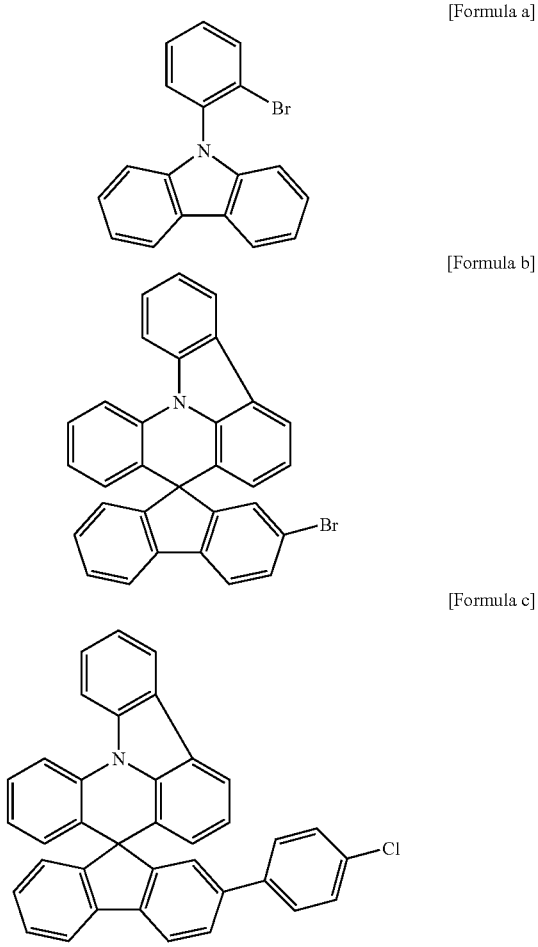

[Formula a]

[Formula b]

[Formula c]

Preparation Example 1

Preparation of a Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature was conducted, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the resulting white solid compound (800 mg, 25% yield). MS: $[M+H]^+=323$.

Preparation Example 2

Preparation of a Starting Material Represented by Formula b 4.19 g of starting material represented by Formula a (13 mmol) were dissolved in 50 ml of purified THF, and 4.8 ml of n-BuLi (2.5 M in hexane, 12 mmol) were slowly dropped thereon at −78° C. Stirring was conducted at the same temperature for 45 min, and 2.59 g of 2-bromo-9-fluorenone (10.0 mmol) were added thereto. After stirring was conducted at the same temperature for 1 hour, the temperature was raised to normal temperature, stirring was carried out for an additional 2 hours, and the reaction was completed in a $NH_4Cl$ aqueous solution. An organic material was extracted with ethyl ether, water was removed therefrom, and an organic solvent was removed to produce yellow solid. The produced solid was dispersed in ethanol, stirred, filtered, and vacuum dried to produce 4.5 g of intermediate material. The intermediate solid was dispersed in 40 ml of acetic acid, 12 drops of concentrated sulfuric acid were added thereto, and reflux was conducted for 3 hours. After cooling to normal temperature, the resulting solid was filtered, washed with ethanol, and vacuum dried to create 3.98 g of product (82.2% yield). MS: $[M+H]^+=484$.

Preparation Example 3

Preparation of a Starting Material Represented by Formula c

The starting material represented by Formula c (5.0 g, 10.32 mmol) was completely dissolved in 40 ml of THF, 4-chloro-phenylboronic acid (2.42 g, 15.48 mmol), 2M potassium carbonate solution, tetrakis(triphenylphosphine) palladium(0) (0.31 mmol, 0.36 g), and 10 ml of ethanol were added thereto, and reflux was conducted for 24 hours. After the reaction was completed, cooling to normal temperature was conducted, and filtration was conducted. Washing was conducted with water and ethanol, several times. Recrystallization was conducted with ethanol, and vacuum drying was conducted to produce a compound (4.97 g, yield 93%). MS: $[M+H]^+=515$.

Example 1

Preparation of the Compound Represented by Formula 2-2

The compound of Formula b (3.0 g, 6.19 mmol) and N-phenyl-1-naphthylamine (1.5 g, 6.81 mmol) were dissolved in 50 ml of toluene, sodium-tert-butoxide (0.89 g, 9.3 mmol), bis(dibenzylidene acetone)palladium(0) ($Pd(dba)_2$, 0.07 g, 0.124 mmol), and 50 wt % tri-tert-butylphosphine (0.09 ml, 0.186 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce a compound (2.0 g, yield 52%). MS: $[M+H]^+=622$.

Example 2

Preparation of the Compound Represented by Formula 3-2

The compound of Formula c (5.0 g, 9.69 mmol) and N-phenyl-1-naphthylamine (2.3 g, 10.5 mmol) were dissolved in 50 ml of toluene, sodium-tert-butoxide (3.02 g, 31.5 mmol), bis(dibenzylidene acetone)palladium(0) (Pd(dba)$_2$, 0.217 g, 0.121 mmol), and 50 wt % tri-tert-butylphosphine (0.13 ml, 0.315 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce a compound (4.2 g, yield 62%). MS: [M+H]$^+$=698.

Example 3

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

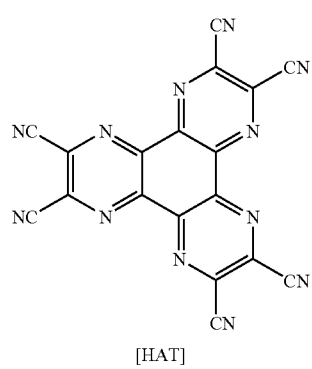

[HAT]

The compound of Formula 2-2 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

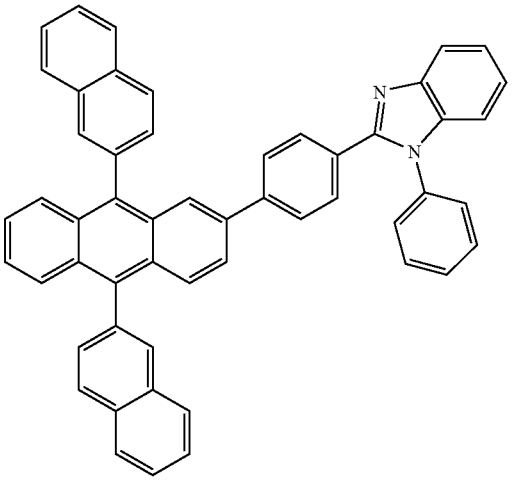

Electron transport layer material

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3 \times 10^{-7}$.

The resulting device had an electric field of 9.74 V at a forward current density of 100 mA/cm$^2$, and a spectrum having a light efficiency of 1.63 lm/W. The operation and light emission of the device at the above-mentioned actuating voltage mean that the compound of Formula 2-2, which formed the layer between the hole injection layer and the light emitting layer, functions to transport holes.

Example 4

Production of an Organic Light Emitting Device

The procedure of example 3 was repeated to produce a device except that the compound of Formula 3-2 was used instead of the compound of Formula 2-2 as a hole transport layer.

The resulting device had an electric field of 8.59 V at a forward current density of 100 mA/cm$^2$, and a spectrum having a light efficiency of 1.79 lm/W. The operation and light emission of the device at the above-mentioned actuating voltage mean that the compound of Formula 3-2, which formed the layer between the hole injection layer and the light emitting layer, functions to transport holes.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:
1. An organic light emitting device, comprising:
a first electrode;
organic material layer(s) comprising a light emitting layer, wherein at least one layer of the organic material layer(s) includes the compound of Formula 1; and
a second electrode;
wherein the first electrode, the organic material layer(s), and the second electrode form layered structure,

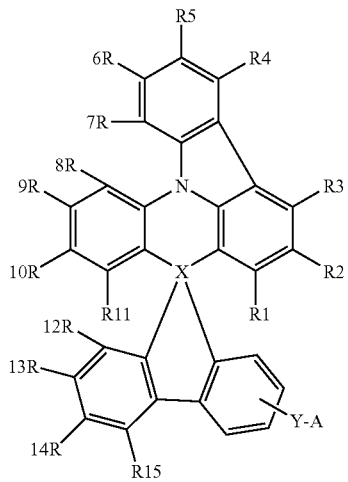

wherein X is C or Si,
A is —NZ1Z2; Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;
Z1 and Z2 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons;
R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group, and R1 to R11 may form aliphatic or hetero condensation rings along with adjacent groups; and R12 to R15 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group, and R12 to R15 may form aliphatic or hetero condensation rings along with adjacent groups; and
R7 and R8 may be directly connected to each other, or may form a condensation ring along with a group selected from the group consisting of O, S, NR, PR, C=O, CRR', and SiRR', wherein R and R' are each independently or collectively hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound.

2. The organic light emitting device as set forth in claim 1, wherein R7 and R8 of Formula 1 form a condensation ring along with a group selected from the group consisting of O, S, NR, PR, C=O, CRR', and SiRR'.

3. The organic light emitting device as set forth in claim 1, wherein the compound of Formula 1 is any one of compounds of Formulae 2 to 5:

[Formula 2]

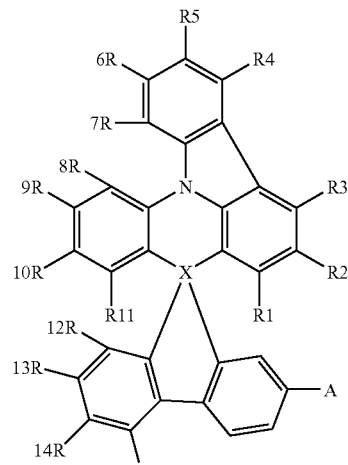

[Formula 3]

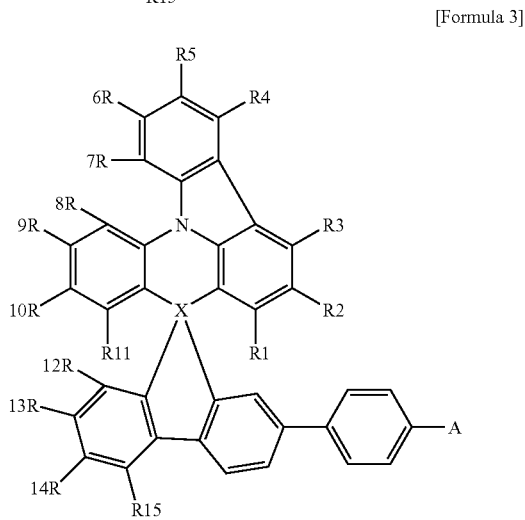

-continued
[Formula 4]
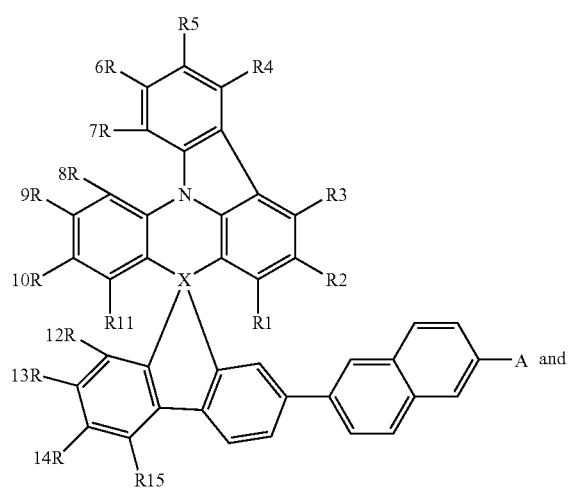
and
[Formula 5]
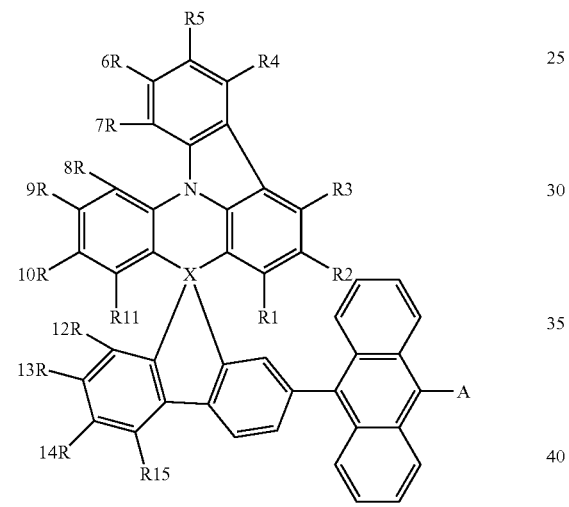
4. The organic light emitting device as set forth in claim 1, wherein A of Formula 1 is any one of following groups:
1
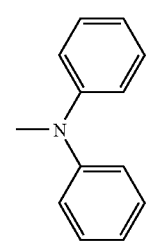
2
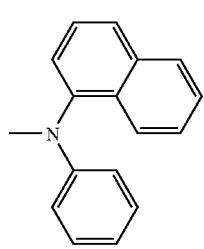
-continued
3
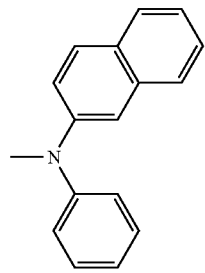
4
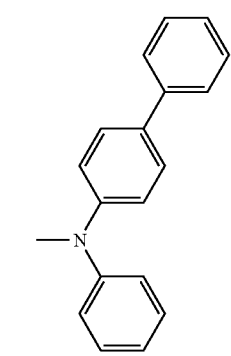
5
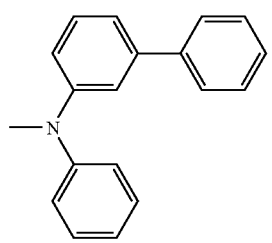
6
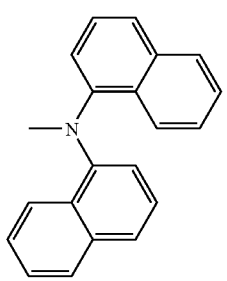
7
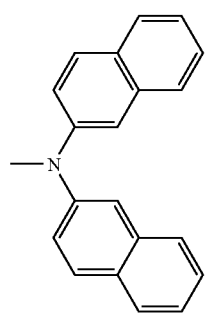

-continued
8
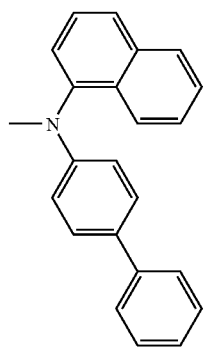
9
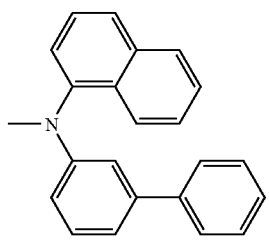
10
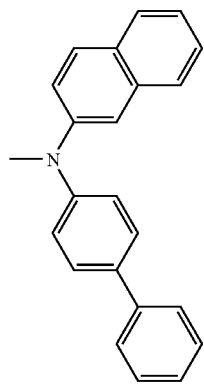
11
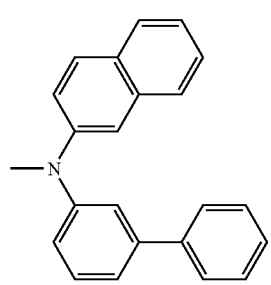
-continued
12
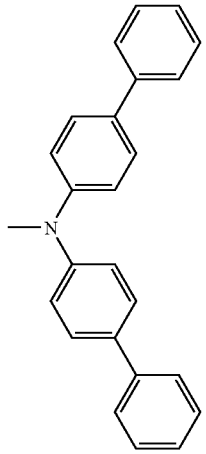
13
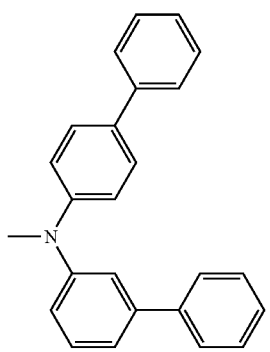
14
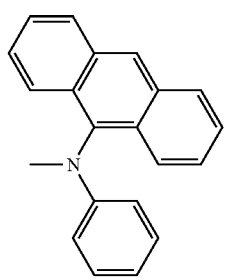
15
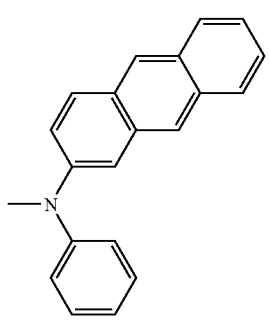

-continued
16
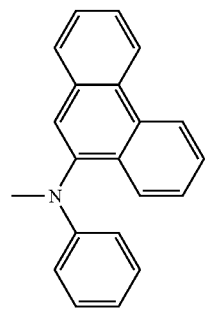
17
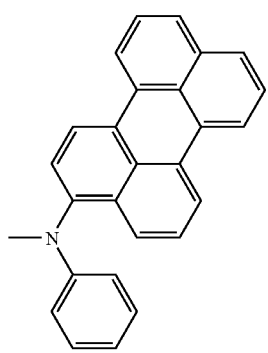
18
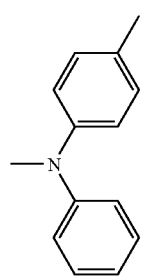
19
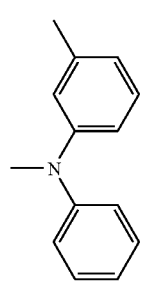
20
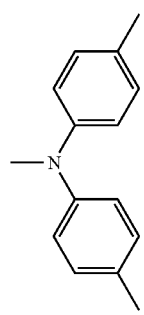
-continued
21
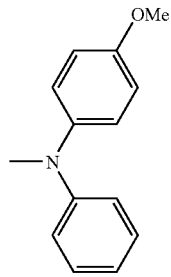
22
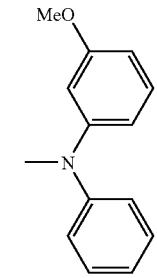
23
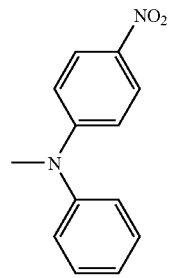
24
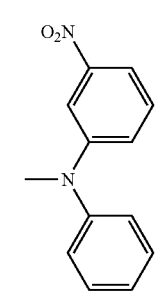
25
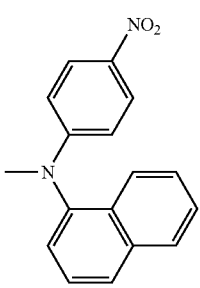

-continued
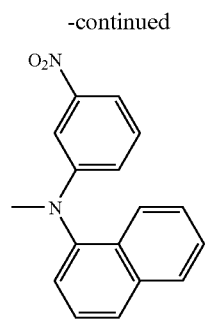
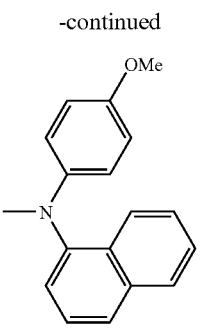

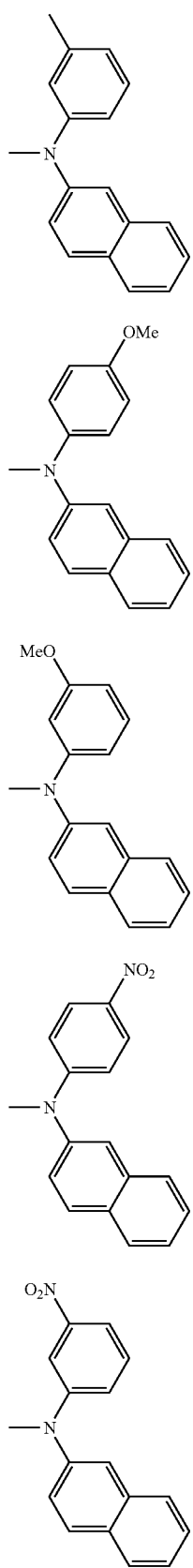
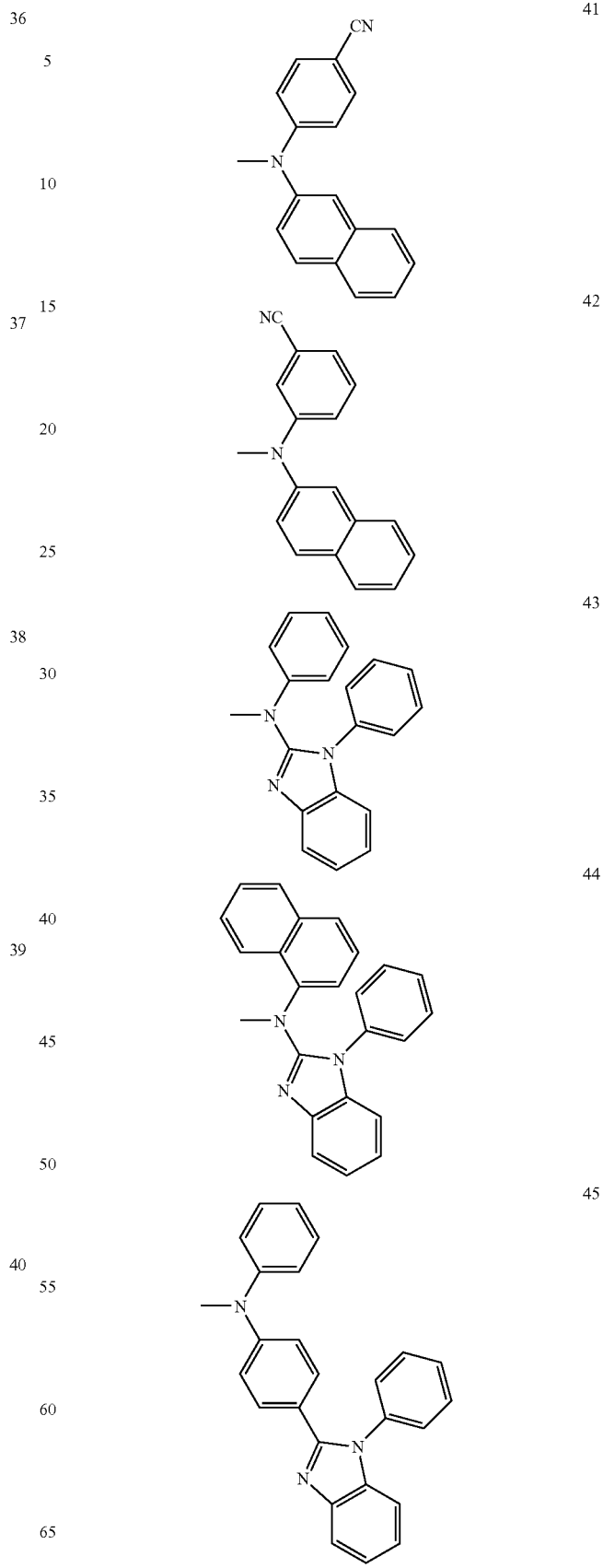

46
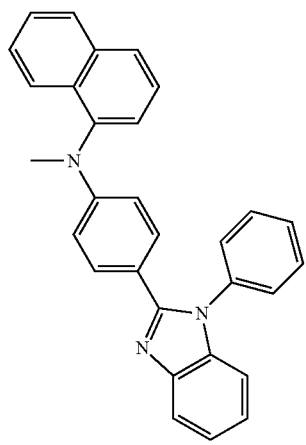
47
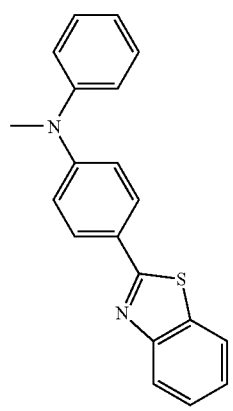
48
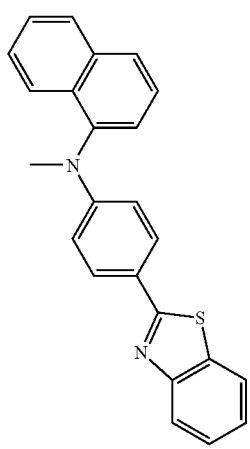
49
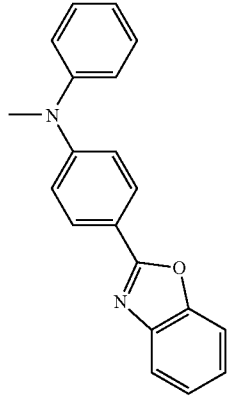
50
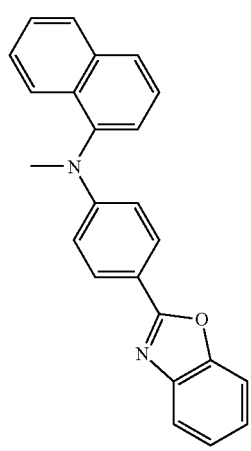
51
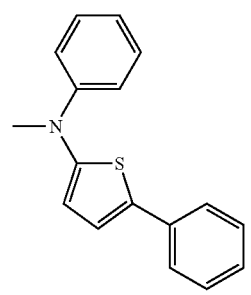
52
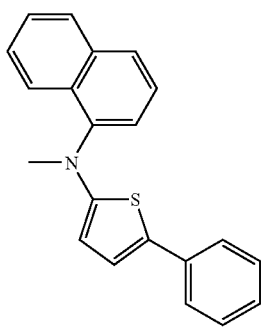

-continued

53 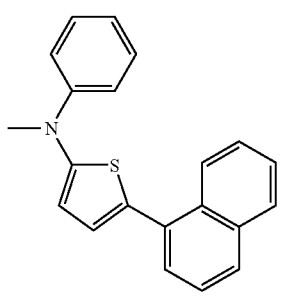

54 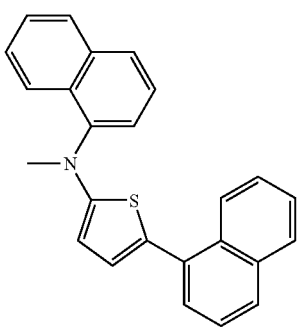

55 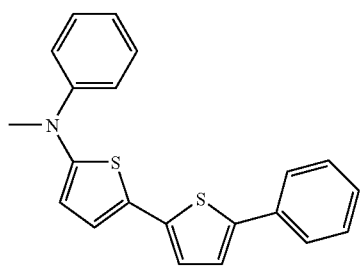

56 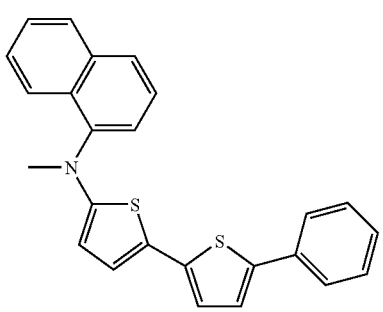

-continued

57 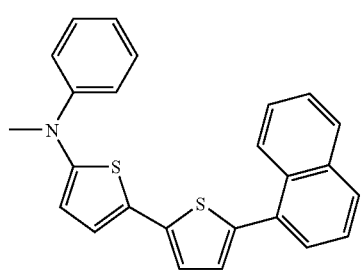

58 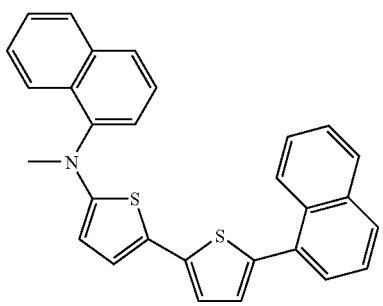

59

60

61

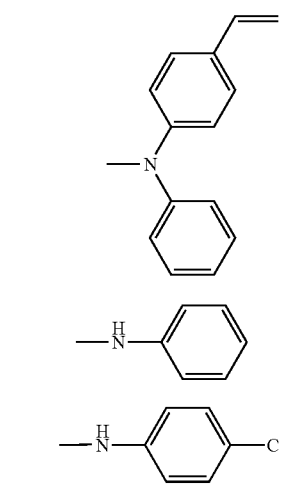

5. The organic light emitting device as set forth in claim 1, wherein the organic material layer(s) comprise a hole transport layer, and the hole transport layer includes the compound of Formula 1.

6. The organic light emitting device as set forth in claim 1, wherein the organic material layer(s) comprise a hole injection layer, and the hole injection layer includes the compound of Formula 1.

7. The organic light emitting device as set forth in claim 1, wherein the organic material layer(s) comprise a layer which both injects and transports holes and which includes the compound of Formula 1.

* * * * *